United States Patent
Akimoto et al.

[11] Patent Number: 5,889,046
[45] Date of Patent: Mar. 30, 1999

[54] METHOD FOR PREVENTING OR ALLEVIATING CEREBRAL APOPLEXY

[75] Inventors: Kengo Akimoto; Shiro Morimoto, both of Osaka; Yasuo Matsumura, Kita Katsuragi-gun; Hajime Yoshizumi; Tetsuo Murakami, both of Nara, all of Japan

[73] Assignee: Suntory Limited, Osaka, Japan

[21] Appl. No.: 595,209

[22] Filed: Feb. 1, 1996

[30] Foreign Application Priority Data

Feb. 1, 1995 [JP] Japan ................................. 7-015276
Mar. 28, 1995 [JP] Japan ................................. 7-070205

[51] Int. Cl.$^6$ ................. A61K 31/335; A61K 31/36; A61K 31/34
[52] U.S. Cl. .................. 514/470; 514/464; 514/452
[58] Field of Search ................. 514/470, 464, 514/452

[56] References Cited

FOREIGN PATENT DOCUMENTS

| | | |
|---|---|---|
| 0 387 000 A2 | 9/1990 | European Pat. Off. . |
| 0 409 654 A3 | 1/1991 | European Pat. Off. . |
| 0 519 673 A1 | 12/1992 | European Pat. Off. . |
| 0 681 788 A2 | 11/1995 | European Pat. Off. . |
| 61-012624 | 1/1986 | Japan . |

*Primary Examiner*—Kimberly Jordan
*Attorney, Agent, or Firm*—Burns, Doane, Swecker & Mathis, L.L.P.

[57] ABSTRACT

The present invention discloses a preventive or ameliorant of hypertension or medical symptoms caused by it and a food or beverage that prevents or ameliorates hypertension or medical symptoms caused by it that contain for its active ingredient dioxabicyclo[3.3.0]octane derivative represented by the formula (2).

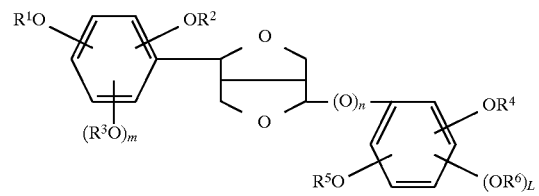

wherein, $R^1$, $R^2$, $R^3$, $R^4$, $R^5$ and $R^6$ are respectively and independently a hydrogen atom or an alkyl group having 1 to 3 carbon atoms, or $R^1$ and $R^2$ and/or $R^4$ and $R^5$ collectively represent a methylene group or ethylene group, and n, m and L represent 0 or 1.

14 Claims, 2 Drawing Sheets

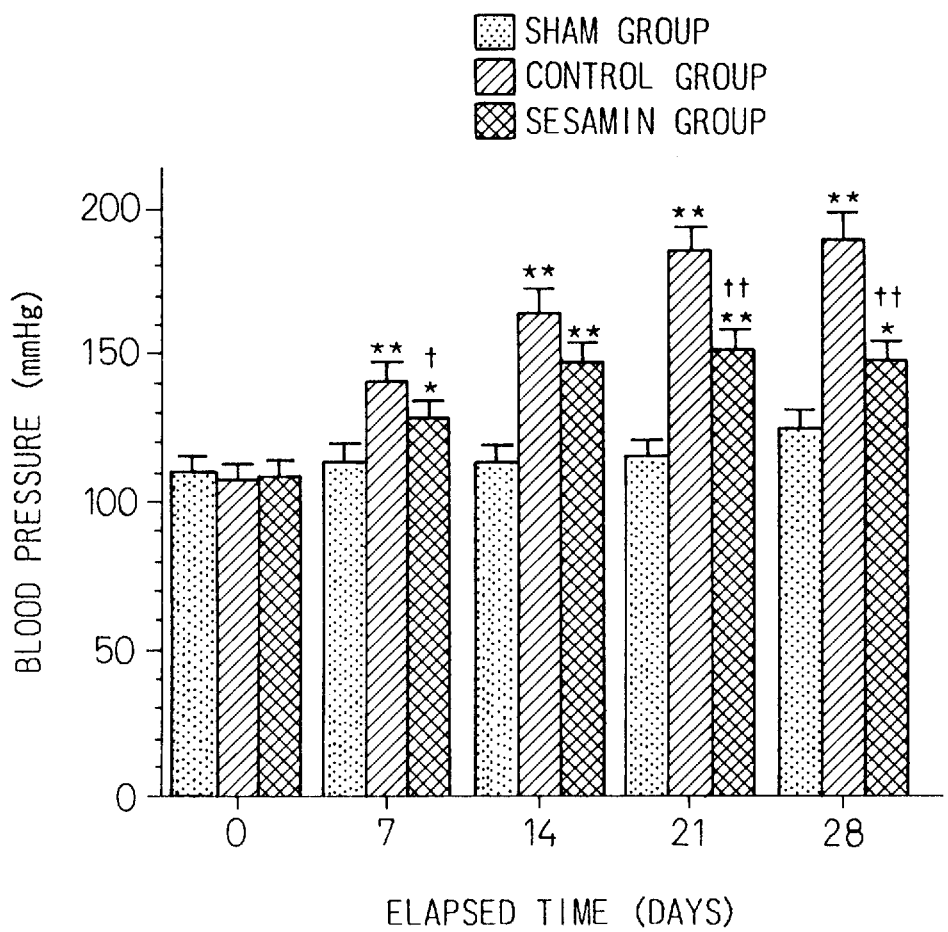

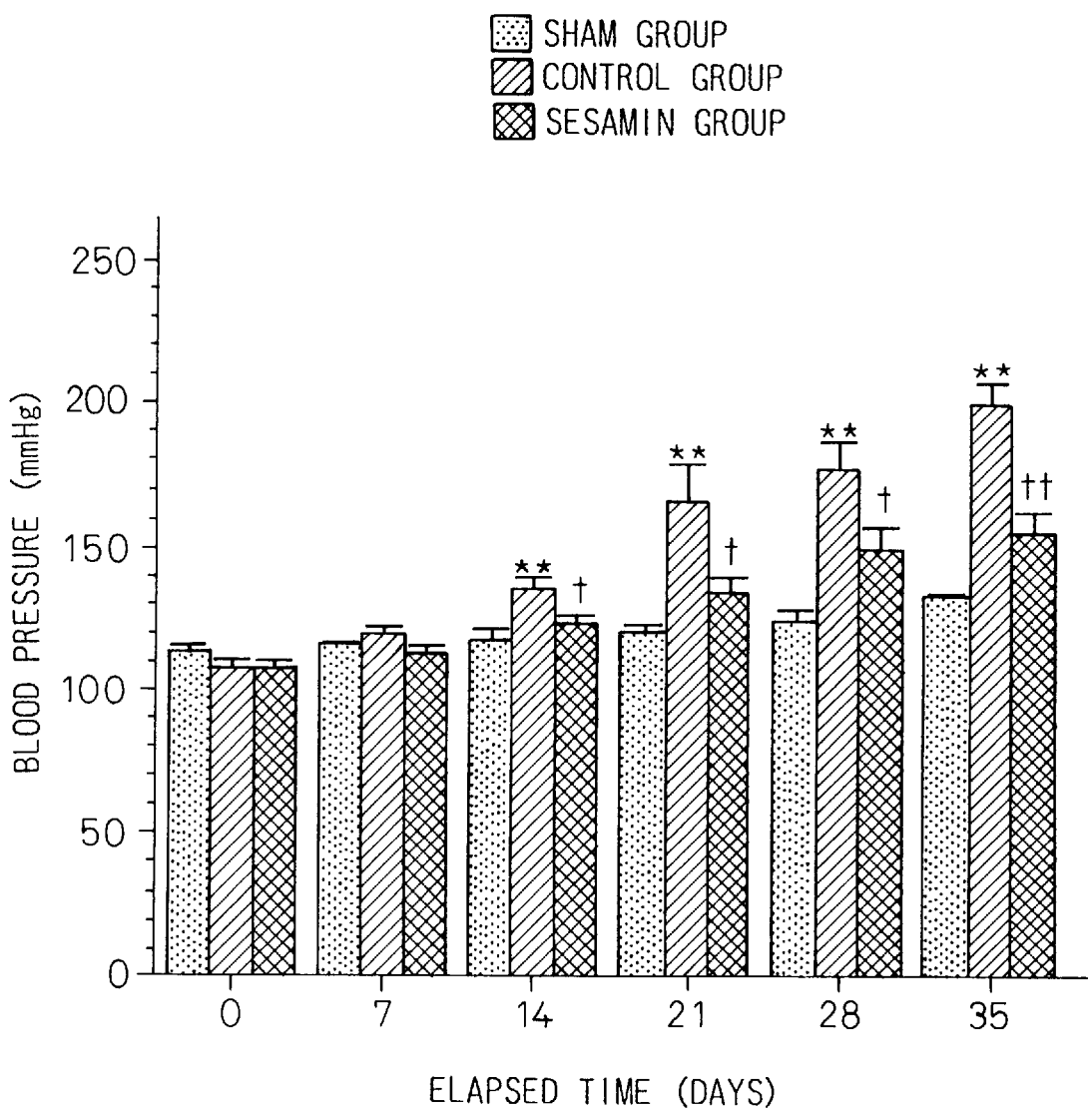

METHOD FOR PREVENTING OR ALLEVIATING CEREBRAL APOPLEXY

BACKGROUND OF INVENTION

1. Field of Invention

The present invention relates to a preventive or alleviative agent for hypertension or medical symptoms caused thereby comprising as its active ingredient a dioxabicyclo[3.3.0] octane derivative, a food or beverage having the effect of preventing or alleviating hypertension or medical symptoms caused thereby comprising a dioxabicyclo[3.3.0]octane derivative or an extract comprising said derivative as its active ingredient, and a process for production thereof.

2. Related Art

Although the condition in which blood pressure remains continuously high is referred to as hypertension, there are considerable differences of opinion in the art with respect to what degree of high blood pressure constitutes hypertension. The World Health Organization (WHO) has made the following criteria based on epidemiological considerations. Namely, the normal range of blood pressure is set at 140/90 mmHg or less, and blood pressure of 160/95 mmHg and above is considered to constitute high blood pressure. However, in addition to a certain degree of correction required according to age and sex, in the clinical setting, there are many practitioners who consider blood pressure in excess of 150/90 mmHg to constitute high blood pressure.

Although there are various diseases that bring about hypertension, these can be broadly classified into essential hypertension, for which the cause is unknown, and secondary hypertension, for which there is a definite cause. Examples of diseases that cause secondary hypertension include kidney diseases such as glomerulonephritis and pyelonephritis, renal artery arctation, endocrine diseases such as primary aldosteronism, Cushing's syndrome (both of which are adrenocortical tumors) and melanocytoma (an adrenomedullary tumor), aortic arctation, certain types of central nervous system diseases and others. On the other hand, essential hypertension is responsible for the largest portion of hypertension cases, accounting for roughly 80% of all hypertension cases. The cause remains unknown at present, and although genetic factors have clearly been shown to be involved, details of the genetic mode are unknown.

Essential hypertension frequently occurs between the ages of 35 and 40. In the beginning, blood pressure is labile, and with the exception of the rise in blood pressure, hypertension does not exhibit any other extraordinary subjective or objective symptoms. With the passage of time, high blood pressure becomes continuous, eventually leading to left ventricular hypertrophy, arteriosclerosis and arteriolosclerosis, and causing ischemic diseases of the brain, heart and kidney. As the patient enters adulthood and old age, hypertension eventually causes death due to cerebral hemorrhage, cerebral thrombosis, congestive heart failure, myocardial infarction or uremia. Thus, hypertension is a disease that has a detrimental effect on various vascular diseases, and in particular, vascular disorders of the heart and brain. The extent to which hypertension can be prevented and treated is therefore an important issue for modern medicine.

At present, although it is possible to lower blood pressure even in the most serious cases of hypertension due to the remarkable progress that has been made in the area of depressors, conversely numerous problems remain to be solved with respect to adverse side effects of these drugs.

Since treatment of hypertension requires drug therapy over an extended period of time (usually the life of the patient), there is a need for a drug that has minimal adverse side effects while offering even greater efficacy. In addition, since the particular depressor that is suitable for an individual may vary even for the same type of hypertension, various types of different depressors are necessary. Moreover, there is also a need for a mild depressor that is essentially free of adverse side effects in cases of hypertension that are not that serious.

On the basis of these viewpoints, research has recently been conducted on a plant extract to be used in pharmaceutical applications that has blood pressure lowering effects. Differing from conventional depressors such as calcium antagonists and β-blockers, this plant extract preparation has hardly any adverse side effects, and is considered to occupy an important position in applications to self-medication. Particularly in the society of today with its extremely high levels of stress, there are many persons suffering from symptoms of stress, which can be considered to be a precursor of hypertension. A natural pharmaceutical preparation that is extremely safe and offers excellent efficacy is needed by these people.

SUMMARY OF INVENTION

Thus, the object of the present invention is to provide a novel preventive or alleviative agent for treatment of hypertension or medical symptoms caused thereby that has a high degree of safety and minimal adverse side effects, a food or beverage having the effect of preventing or alleviating hypertension or medical symptoms caused thereby, and a process for production thereof.

As a result of conducting various research to achieve the above-mentioned object, the inventors of the present invention found that a dioxabicyclo[3.3.0]octane derivative, extracted or isolated from sesame seeds, sesame lees or sesame oil and so forth, or synthesized, is effective in preventing or alleviating hypertension or medical symptoms caused thereby.

Thus, the present invention provides a preventive or alleviative agent for treatment of hypertension or medical symptoms caused thereby comprising as its active ingredient a dioxabicyclo[3.3.0]octane derivative represented by the following general formula (I):

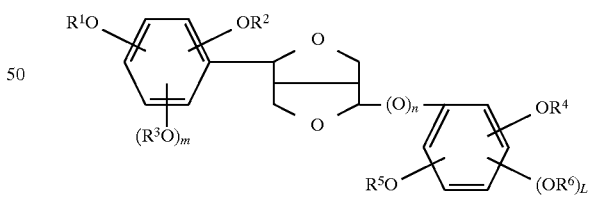

wherein, $R^1$, $R^2$, $R^3$, $R^4$, $R^5$ and $R^6$ are respectively and independently a hydrogen atom or an alkyl group having 1 to 3 carbon atoms, or $R^1$ and $R^2$ and/or $R^4$ and $R^5$ collectively represent a methylene group or ethylene group, and n, m and L represent 0 or 1.

In addition, the present invention provides a food or beverage having the effect of preventing or alleviating hypertension or medical symptoms caused thereby comprising a dioxabicyclo[3.3.0]octane derivative represented by the general formula (1) below, or an extract comprising as its active ingredient said derivative;

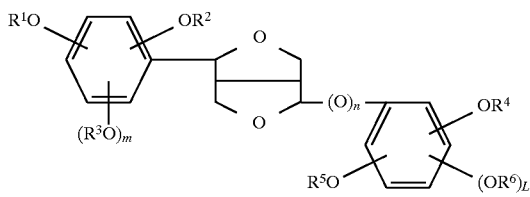

wherein, $R^1$, $R^2$, $R^3$, $R^4$, $R^5$ and $R^6$ are respectively and independently a hydrogen atom or an alkyl group having 1 to 3 carbon atoms, or $R^1$ and $R^2$ and/or $R^4$ and $R^5$ collectively represent a methylene group or ethylene group, and n, m and L represent 0 or 1.

Moreover, the present invention also provides a food or beverage, and a process for production thereof, having the effect of preventing or alleviating hypertension or medical symptoms caused thereby, by adding sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, or 2-(3,4-methylenedioxyphenyl)-6-(3-methoxy-4-hydroxyphenoxy)-3,7-dioxabicyclo[3.3.0]octane, or an extract having for its active ingredient one or a plurality of said compounds to a food or beverage essentially not containing sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, or 2-(3,4-methylenedioxyphenyl)-6-(3-methoxy-4-hydroxyphenoxy)-3,7-dioxabicyclo[3.3.0]octane, either alone or in the form of a mixture.

BRIEF DESCRIPTION OF THE DRAWINGS

FIG. 1 is a graph showing the blood pressure lowering effect of sesamin and so forth in renal hypertension model rats.

FIG. 2 is a graph showing the blood pressure lowering effect of sesamin and so forth in sodium-induced hypertension model rats.

DETAILED DESCRIPTION

The dioxabicyclo[3.3.0]octane derivative, which is the active ingredient of the present invention, is a compound represented with the following general formula (I):

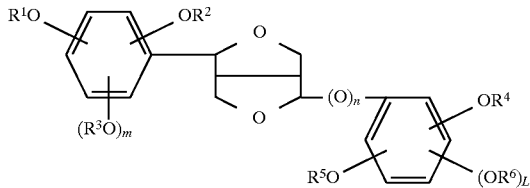

wherein, $R^1$, $R^2$, $R^3$, $R^4$, $R^5$ and $R^6$ are respectively and independently a hydrogen atom or an alkyl group having 1 to 3 carbon atoms, or $R^1$ and $R^2$ and/or $R^4$ and $R^5$ collectively represent a methylene group or ethylene group, and n, m and L represent 0 or 1. Examples of alkyl groups having 1 to 3 carbon atoms includes a methyl group, ethyl group, n-propyl group and isopropyl group.

More specifically, examples of said dioxabicyclo[3.3.0] octane derivative include compounds such as sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane and 2-(3,4-methylenedioxyphenyl)-6-(3-methoxy-4-hydroxyphenoxy)-3,7-dioxabicyclo[3.3.0]octane. These compounds may be in the form of glycosides. The enantiomers of the above-mentioned compounds are also included in the present invention.

In the present invention, the above-mentioned dioxabicyclo[3.3.0]octane derivative (to be referred to as the derivative of the present invention) can be used either alone or by combining two or more types. In addition, the derivative of the present invention is not limited to a highly pure substance in the present invention, but rather an extract can also be used that has for its active ingredient one or a plurality of types of the above-mentioned dioxabicyclo [3.3.0]octane derivative (to be referred to as the extract of the present invention).

The extract of the present invention can be extracted in accordance with routine methods from a naturally-occurring substance that contains the derivative of the present invention. Examples of naturally-occurring substances that contain the derivative of the present invention include sesame oil, sesame lees, by-products of the sesame oil production process, sesame seeds, an extract of Gokahi derived from a medicinal plant which is *Acanthopanax gracilistylus* W. W. Smith, *Acanthopanax sessiliflorus* Seem., *Acanthopanax senticosus* Harms, *Acanthopanax henryi* Harms, or *Acanthopanax verticillatus* Hoo; an extract of Toboku derived from a medicinal plant which is *Paulownia fortunei* Hemsl or *Paulownia tomentosa* Stend.; an extract of Hakukajuhi derived from a medicinal plant which is *Ginkgo biloba* L.; an extract of Hihatsu derived from a medicinal plant which is *Piper longum* L.; or an extract of Saishin (Asiasari radix) derived from a medicinal plant which is *Asarum heterotropoides* F. Schm. var. *mandshuricum* Kitag., or *Asarum sieboldii* Mig.

In addition, the content of the derivative of the present invention in the extract of the present invention is at least 0.1 wt %, preferably at least 1.0 wt % and more preferably at least 5.0 wt %. Needless to say, a larger amount of the present derivative contained in the extract is better, and in this case, especially in a food or beverage, an amount of the extract can be reduced, and the effect of compounds other than the active ingredient may be reduced. In particular, the total content of sesamin and episesamin is at least 0.05 wt %, preferably at least 0.5 wt %, and more preferably at least 2.0 wt %.

For example, in order to obtain an extract of the present invention from sesame oil, extraction and concentration can be performed by using various organic solvents that are essentially immiscible with sesame oil and are able to extract and dissolve the derivative of the present invention (examples of which include acetone, methyl ethyl ketone, diethyl ketone, methanol and ethanol).

One example of a process for obtaining an extract of the present invention from sesame oil comprises the steps of uniformly mixing sesame oil with either of the above-mentioned solvents, allowing to stand undisturbed at a low temperature, performing phase separation in accordance with routine methods such as centrifugal separation, and distilling off the solvent from the solvent fraction. More specifically, after dissolving sesame oil in 2 to 10 volumes, and preferably 6 to 8 volumes, of acetone, the solution is allowed to stand undisturbed overnight at −80° C. After the oil components have settled as a result of the above, acetone is removed by distillation from the filtrate obtained by filtration to obtain an extract of the present invention.

In addition, another example of a process for obtaining the extract of the present invention from sesame oil comprises the steps of mixing sesame oil with hot methanol or hot ethanol, allowing to stand undisturbed at room temperature and removing by evaporation the solvent from the solvent fraction. More specifically, after vigorously mixing sesame oil with 2 to 10 volumes, and preferably 5 to 7 volumes, of hot methanol (50° C. or higher) or hot ethanol (50° C. or higher), the mixture is allowed to stand undisturbed at room temperature or phase separation is performed in accordance with routine methods such as centrifugal separation followed by removal by distillation of the solvent from the solvent fraction to obtain an extract of the present invention.

Moreover, an extract of the present invention can also be obtained by using supercritical gas extraction.

The sesame oil that is used may either be a refined product or an unrefined product used prior to the discoloration step during the production of sesame oil.

In addition, in order to obtain an extract of the present invention from sesame seeds or sesame lees (defatted sesame seeds containing a residual oil content of 8 to 10%), after crushing the sesame seeds or sesame lees as necessary, extraction can be performed in accordance with conventional methods using any solvent such as any of the same solvents used in the extraction from sesame oil described above. After separating an extraction residue, the extract is obtained by removing the solvent from the extract liquid by evaporation and so forth.

The derivative of the present invention can be isolated from sesame oil extract, sesame lee extract or sesame seed extract prepared in accordance with the processes described above, by treating in accordance with conventional methods such as column chromatography, high-performance liquid chromatography, recrystallization, distillation or liquid-liquid exchange distribution chromatography or the like. More specifically, after separating the above-mentioned extract with high-performance liquid chromatography using a reverse phase column ($5C_{18}$) and methanol/water (60:40) for the eluate, and distilling off the solvent, the resulting crystals are recrystallized with ethanol to obtain the derivative of the present invention such as sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, or 2-(3,4-methylenedioxyphenyl)-6-(3-methoxy-4-hydroxyphenoxy)-3,7-dioxabicyclo[3.3.0]octane. Furthermore, the process and refining process for obtaining the derivative of the present invention and the extract of the present invention are not limited to these processes.

In addition, the derivative of the present invention can also be obtained by synthesis in accordance with conventional methods.

For example, in addition to sesamin and episesamin which can be synthesized using the method of Beroza et al. [(J. Am. Chem. Soc. 78, 1242 (1956)], pinoresinol ($R^1=R^4=H$, $R^2=R^5=CH_3$ and n=m=l=0 in the general formula (I)) can be synthesized according to the method of Freundenberg et al. [Chem. Ber., 86, 1157 (1953)], while syringaresinol ($R^1=R^4=H$, $R^2=R^3=R^5=R^6=CH_3$, n=0 and m=l=1 in the general formula (I)) can be synthesized according to the method of Freundenberg et al. [Chem. Ber., 88, 16 (1955)].

Moreover, the derivative of the present invention or the extract of the present invention can be used in combination with an antioxidant. Examples of antioxidants include natural antioxidants such as tocopherols, flavone derivatives, phyllodulcins, kojic acid, gallic acid derivatives, catechins, fukinolic acid gossypol, pyrazine derivatives, sesamol, guaiacol, guaic resin, p-coumalic acid, nor-dihydroguaiaretic acid, sterols, terpens, nucleic acid bases and carotenoids, or synthetic antioxidants represented by compounds such as butylhydroxyanisole (BHA), butylhydroxytoluene (BHT), monotertiary-butylhydroxyquinone (TBHQ) and 4-hydroxymethyl-2,6-ditertiary-butylphenol (HMBP).

Tocopherols are particularly preferable antioxidants, examples of such including α-tocopherol, β-tocopherol, γ-tocopherol, δ-tocopherol, ε-tocopherol, ζ-tocopherol, η-tocopherol and tocopherol esters (such as tocopherol acetate). Moreover, examples of carotenoids include β-carotene, canthaxanthin and astaxanthin.

Although there are no particular restrictions on the ratios of the derivative of the present invention and antioxidant when used in combination, no less than 0.001 parts by weight and no more than 1000 parts by weight of antioxidant per 1 part by weight of the derivative of the present invention is preferable. Moreover, a range of 0.01 to 100 parts by weight is more preferable, while a range of 0.029 to 40 parts by weight is still more preferable.

Since the derivative of the present invention or extract of the present invention significantly suppresses increases in blood pressure with minimal adverse side effects, it is effective in the prevention or alleviation of essential or secondary hypertension and medical symptoms caused thereby. In addition, examples of medical symptoms that are caused by high blood pressure include left ventricular hypertrophy, arteriosclerosis, arteriolosclerosis, ischemic disorders of the brain, heart and kidney (for example, cerebral apoplexy, angina pectoris and myocardial infarction), as well as cerebral hemorrhage, cerebral thrombosis, congestive heart failure and uremia that occur in adulthood and old age. Furthermore, in the present invention, alleviation of symptoms is used in the broad sense, and includes treatment of diseases.

In the case of using the derivative of the present invention as a pharmaceutical, the drug form may be any form provided it can be given orally or parenterally as necessary. Examples of such drug forms include injection solutions, infusion solutions, powders, granules, tablets, capsules, pills, troches, internal liquids, suspensions, emulsions, syrups, external liquids, packs, nasal drops, ear drops, eye drops, inhalants, ointments, lotions and suppositories. These can be used either alone or in combination according to the symptoms.

Each of these preparations can be prepared using known adjuvants that can be conventionally used in the field of pharmaceutical formulation technology, such as vehicles, binders, preservatives, stabilizers, disintegration agents, lubricants and correctives, in combination with the primary drug corresponding to the objective of treatment in accordance with conventional methods. For example, in the case of preparing an injection, a solubilizer for use with pharmaceuticals, such as a nonionic surface activator, can be used. More specifically, the derivative of the present invention is heated and dissolved in 80 volumes of a nonionic surface activator such as POE(60) cured castor oil or POE sorbitan monooleate and then prepared by diluting with physiological saline. In addition, suitable isotonic agents, stabilizers, preservatives and analgesics may also be added as necessary.

As examples of external preparations, ointments, creams and so forth can be prepared in accordance with conventional methods using Vaseline, paraffin, oils, lanolin or macrogol and so forth for the base. Although the dose varies according to the objective of administration and the condition of the patient to be administered (sex, age, body weight and so forth), normally in the case of oral administration to adults, the dose is within the range of 1 mg to 10 g, preferably 1 mg to 2 g and more preferably 1 mg to 200 mg per day as the total amount of derivative of the present invention. In the case of parenteral administration, the dose is within the range of 0.1 mg to 1 g, preferably 0.1 mg to 200 mg and more preferably 0.1 mg to 100 mg per day as the total amount of derivative of the present invention, the dose being suitably adjusted in each case.

In addition, since the preventive or alleviative effects on hypertension or medical symptoms caused thereby possessed by the derivative of the present invention are enhanced by administration with antioxidant, and tocopherols in particular, although varying according to the objective of administration and the condition of the patient being administered (sex, age, body weight and so forth), the dose of the derivative of the present invention in the case of oral administration to adults is normally within the range of 0.1 mg to 2 g, preferably 0.1 mg to 500 mg and more preferably 0.1 mg to 100 mg per day as the total amount of derivative of the present invention. In addition, the dose in the case of parenteral administration to adults is normally within the range of 0.01 mg to 200 mg, preferably 0.01 mg to 50 mg and more preferably 0.01 mg to 20 mg per day as the total amount of derivative of the present invention. Moreover, the blending ratio of the derivative of the present invention and antioxidant is 0.001 to 1000 parts by weight, preferably 0.01 to 100 parts by weight and more preferably 0.029 to 40 parts by weight of antioxidant to 1 part by weight of the derivative of the present invention, the doses being suitably adjusted in each case.

Since the derivative of the present invention is a compound or analogous compound found in conventional foods, it is clear that it has excellent stability. In addition, this is also clear since there were no abnormal symptoms observed whatsoever when 2.14 g/day/kg of sesamin was administered orally for two consecutive weeks to 7 week old, IRC male mice.

In the case of using the derivative of the present invention or an extract of the present invention as a food or beverage, its form may be any of the forms of the above-mentioned pharmaceutical preparations, or in the form of a solid or liquid food product or sweets, examples of which include agricultural food products such as bread, noodles, rice, confections (including cookies, cake, candy, chocolate and Japanese style confections), tofu (soybean curd) and their processed foods, fermented food products such as Japanese sake, medicinal alcoholic beverages, sweet sake (alcoholic product for cooking), vinegar, soy sauce and soypaste (miso), edible oil and fat food products such as salad dressing, mayonnaise, margarine, shortening and edible fat and oil, livestock food products such as yogurt, ham, bacon and sausage, marine food products such as boiled fish paste, steamed fish paste, fried fish paste, and beverages such as fruit juice, carbonated beverages, sports drinks, alcoholic beverages and tea.

In addition, in the case of using the derivative of the present invention or an extract thereof as a health food or functional food, although the form may be the same as that of the pharmaceutical preparations and foods and beverages described above, it may also be in the form of, for example, processed foods such as liquid foods, semi-digested nutritional foods, component nutritional foods and drinks blended with protein (although proteins such as lactoprotein, soybean protein and egg white albumin, which have balanced amino acids and high nutritional value, are widely used for the protein source, their degradation products, egg white oligopeptides, soybean hydrolysates as well as mixtures of individual amino acids are also used), sugar, fat, trace elements, vitamins, emulsifiers and fragrances, as well as capsules and particles.

The food or beverage of the present invention can be processed and manufactured by adding a prescribed amount of the derivative of the present invention or extract of the present invention to a raw food product essentially not containing the derivative of the present invention, using conventional manufacturing methods. Although varying according to the drug form or form properties of the food product, the amount blended is, in general, preferably 0.001 to 50%, although not limited to this amount. In addition, in the case of ingestion in the form of a health food or functional food when used for the prevention and alleviation of hypertension or medical symptoms caused thereby, the derivative of the present invention or extract of the present invention can be added to any food essentially not containing the derivative of the present invention when preparing hospital meals under the supervision of a nutritionist based on the diet regimen prescribed by the physician, and can be given to patients in the form of a functional food prepared at the hospital.

In the present invention, although examples of a food or beverage essentially not containing the derivative of the present invention refers to foods or beverages that do not have sesame and so forth for their raw material, even if the food or beverage does contain sesame and so forth, those foods or beverages in which the total content of the derivative of the present invention is less than 0.1 mg and preferably 0.8 mg or less per amount of the food or beverage ingested per day, or those foods and beverages in which the total content of sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0] octane, 2,6-bis-(3-methoxy-4-hydroxyphenyl)-3,7-dioxabicyclo[3.3.0]octane, or 2-(3,4-methylenedioxyphenyl)-6-(3-methoxy-4-hydroxyphenoxy)-3,7-dioxabicyclo[3.3.0]octane is less than 0.mg and preferably 0.8 mg or less per amount of the food or beverage ingested per day, are included in those foods and beverages essentially not containing the derivative of the present invention.

In the case of using for the purpose of preventing or alleviating hypertension or medical symptoms caused thereby as well as for maintaining health, it is preferable that the derivative of the present invention be ingested orally within the range of 1 mg to 10 g, preferably 1 mg to 2 g and more preferably 1 mg to 200 mg per day as a general rule.

Moreover, since the preventive or alleviative effects on hypertension or medical symptoms caused thereby as well as effects of maintaining health possessed by the derivative of the present invention are enhanced by combined ingestion of antioxidant, and tocopherols in particular, it is preferable that the derivative of the present invention or extract of the present invention be ingested orally within the range of 0.1 mg to 2 g, preferably 0.1 mg to 500 mg and more preferably 0.1 mg to 100 mg per day as the total amount of derivative of the present invention, and that the blending ratio of the derivative of the present invention and antioxidant is 0.001 to 1000 parts by weight, preferably 0.01 to 100 parts by weight and more preferably 0.029 to 40 parts by weight of antioxidant to 1 part by weight of the derivative of the present invention.

Furthermore, in the case of adding the derivative of the present invention or extract of the present invention to a food or beverage essentially not containing the derivative of the present invention but containing antioxidant, and particularly tocopherols, the derivative of the present invention or extract of the present invention can be added so that the content ratio of the derivative of the present invention and antioxidant in the final form of the food or beverage is 0.01 to 1000 parts by weight, preferably 0.01 to 100 parts by weight and more preferably 0.029 to 40 parts by weight of antioxidant to 1 part by weight of the derivative of the present invention. At this time, an antioxidant can be further added as necessary.

EXAMPLES

The following provides a more detailed explanation of the present invention through Examples.

Example 1

26 male Sprague-Dawley (SD) rats (body weight: 200 to 240 g) were divided into 3 groups. Silver clips (inner diameter: 0.2 mm) were attached to the left renal artery of the rats of 2 of the 3 groups to prepare a two-kidney, one-clip (2K, 1C) renal hypertension model. These rats were further divided into a normal diet group (control group, 10 rats) and a sesamin-containing diet group (sesamin group, 11 rats). The control group was fed a normal diet (commercial type NMF, Oriental Yeast Co., Ltd.), while the sesamin group was given the same diet containing 1% of a mixture of the dioxabicyclo[3.3.0]octane derivatives of the present invention (sesamin: 51.5%, episesamin: 47.8%, and other dioxabicyclo[3.3.0]octane derivatives: 1.1%). The remaining group was used as a non-loaded control group (sham group, 5 rats) and were housed while receiving a normal diet. The blood pressure of each rat was measured using the tail cuff method once a week. Those results are shown in FIG. 1.

TABLE 1

|  | | 2k, 1c | |
| --- | --- | --- | --- |
|  | Sham | Control | Sesamin |
| Body weight (g) | 398.20± 11.83 | 302.30 ± 16.44** | 307.27 ± 11.34** |
| Heart weight (mg) | 1074.80± 40.29 | 1112.90 ± 55.94 | 999.82 ± 51.54 |
| Left ventricle weight + septum weight (mg) | 728.40± 29.73 | 816.10 ± 39.66 | 732.55 ± 39.06 |
| Heart weight/body weight (mg/g) | 2.70± 0.04 | 3.71 ± 0.15** | 3.24 ± 0.08**+ |
| (Left ventricle weight + septum weight)/body weight (mg/g) | 1.83± 0.02 | 2.72 ± 0.09** | 2.37 ± 0.07**++ |

**: $P < 0.01$ with respect to the sham group
+: $P < 0.05$ with respect to the control group
++: $P < 0.01$ with respect to the control group Moreover, after housing rats for 4 weeks, the hearts were excised to investigate the effect on cardiac hypertrophy. Those results are shown in Table 1. The increases in blood pressure and formation of cardiac hypertrophy observed in the control group were significantly inhibited by administration of sesamin.

Example 2

21 male SD rats (6 weeks old) were anesthetized with sodium pentobarbital (40 mg/kg, i.p.) and the right kidney was removed via a right flank incision. After a 1-week postsurgical period, rats were separated into a sham-operated group (sham group) and DOCA-salt group. The latter was further separated into a normal diet group (control group) and a sesamin-containing diet group (sesamin group). Rats of the DOCA-salt group were administrated deoxycorticosterone acetate (DOCA) by subcutaneous injection (15 mg/kg, twice/week) and ingested 1% NaCl to prepare a DOCA-Na-induced hypertension model. These rats were further divided into a normal diet group (control group, 7 rats) and a sesamin-containing diet group (sesamin group, 8 rats).

The rats of the control group and sesamin group were given the same feed as that used in Example 1. The remaining rats were used as a non-loaded control group (sham group, 6 rats) and were housed while receiving a normal diet. The blood pressure of each rat was measured using the tail cuff method once a week. Those results are shown in FIG. 2. Moreover, the hearts of the rats were excised after 5 weeks of housing to investigate the effect on cardiac hypertrophy. Those results are shown in Table 2.

TABLE 2

|  |  | DOCA-Na | |
| --- | --- | --- | --- |
|  | Sham | Control | Sesamin |
| Body weight (g) | 421.83± 8.42 | 331.43 ± 12.23** | 328.75 ± 13.85** |
| Heart weight (mg) | 1101.67± 31.14 | 1217.29 ± 29.15 | 1056.62 ± 60.49+ |
| Left ventricle weight + septum weight (mg) | 739.67± 20.96 | 932.00 ± 22.07** | 779.50 ± 43.23++ |
| Heart weight/body weight (mg/g) | 2.61± 0.05 | 3.71 ± 0.18** | 3.21 ± 0.10**+ |
| (Left ventricle weight + septum weight)/body weight (mg/g) | 1.75± 0.03 | 2.84 ± 0.14** | 2.37 ± 0.07**++ |

**: $P < 0.01$ with respect to the sham group
+: $P < 0.05$ with respect to the control group
++: $P < 0.01$ with respect to the control group The thoracic aorta and mesenteric artery were excised from a suitable number of rats from each group to investigate the effect on vascular hypertrophy. After fixing the thoracic aorta and mesenteric artery excised from rats of each group in formalin, the fixed samples were embedded in paraffin and tissue specimens (5 μgm) were prepared from six locations of the thoracic aorta and 3 locations of the mesenteric artery for each vessel. Each specimen was stained with Elastica-Van-Gieson stain and examined for vascular wall thickness, vascular wall area and the ratio of vascular wall area to lumen area using an image analyzer (IBASII, Carl Zeiss Co., Ltd.). Those results are shown in Table 3.

TABLE 3

Effect of Sesamin on Vascular hypertrophy in DOCA-Na-Induced Hypertension Model Rats

|  | No. of Animals | Vascular Wall Thickness (mm) | Vascular Wall Surface Area ($mm^2$) | Vascular Wall Surface Area/ Lumen Surface Area |
| --- | --- | --- | --- | --- |
| Thoracic Aorta | | | | |
| Sham | 4 | 95 ± 1 | 0.41 ± 0.01 | 0.27 ± 0.01 |
| DOCA-Na (Control) | 3 | 136 ± 5*** | 0.63 ± 0.04** | 0.35 ± 0.02** |
| DOCA-Na (Sesamin) | 5 | 107 ± 4++ | 0.48 ± 0.03* | 0.28 ± 0.01* |

TABLE 3-continued

Effect of Sesamin on Vascular hypertrophy in DOCA-Na-Induced Hypertension Model Rats

|  | No. of Animals | Vascular Wall Thickness (mm) | Vascular Wall Surface Area (mm$^2$) | Vascular Wall Surface Area/ Lumen Surface Area |
|---|---|---|---|---|
| Mesenteric Artery | | | | |
| Sham | 4 | 56 ± 1 | 0.12 ± 0.003 | 0.33 ± 0.02 |
| DOCA-Na (Control) | 3 | 89 ± 2*** | 0.24 ± 0.01*** | 0.49 ± 0.02** |
| DOCA-Na (Sesamin) | 5 | 73 ± 3*,++ | 0.16 ± 0.01**,+++ | 0.42 ± 0.02* |

*: $P < 0.05$, : $P < 0.01$, *: $P < 0.001$ with respect to the sham group
+: $P < 0.05$, ++: $P < 0.001$, +++: $P < 0.001$ with respect to the control group.

The increases in blood pressure, formation of cardiac hypertrophy and vascular hypertrophy observed in rats of the normal diet group were significantly inhibited by administration of sesamin.

Example 3

Silver clips (inner diameter: 0.2 mm) were attached to the left renal artery of male SD rats (body weight: 200–240 g) to prepare a 2K, 1C renal hypertension model. The rats were then assigned to 6 groups of 7 animals each. Rats of one of the groups were given normal diet (commercial type NMF, Oriental Yeast Co., Ltd.). Rats of the remaining 5 groups were respectively fed the same diet containing 1% of sesaminol prepared from refined sesame oil (Compound A), sesamolin prepared from unrefined sesame oil (Compound B), and 2-(3,4-methylenedioxyphenyl)-6-(3-methoxy-4-hydroxyphenyl)-3,7-dioxabicyclo[3.3.0]octane(Compound C), 2,6-bis-(3-methoxy-4-hydroxyphenyl)-3,7-dioxabicyclo[3.3.0]octane (Compound D) and 2-(3,4-methylenedioxyphenyl)-6-(3-methoxy-4-hydroxyphenoxy)-3,7-dioxabicyclo[3.3.0]octane (Compound E), all prepared from an acetone extract of sesame seeds. After 4 weeks, the blood pressure of each rat was measured using the tail cuff method once a week. The blood pressure of animals of the normal diet group increased to 185.4±7.3 mmHg, while blood pressure values of those rats in the groups given feed containing compounds A, B, C, D and E improved to 151.3±6.6, 159.7±7.1, 163.2±8.3, 156.4±5.4 and 162.0±5.9 mmHg, respectively.

Example 4

2.4 g of the mixture of derivatives of the present invention used in Example 1 were added to 100 g of butter fat from which butter milk had been removed in the churning procedure of a butter manufacturing process followed by working to obtain a uniform composition that yielded a butter having the effect of preventing or ameliorating hypertension as a result of adding the active ingredient of the present invention.

Example 5

0.5 g of the derivative of the present invention were mixed with 20.5 g of silicic anhydride followed by the addition of 79 g of cornstarch and further mixing. 100 ml of a 10% hydroxypropylcellulose ethanol solution were added to this mixture followed by heating, extrusion and drying in accordance with routine methods to obtain granules.

Example 6

7 g of the derivative of the present invention were mixed with 20 g of silicic anhydride followed by the addition of 10 g of microcrystalline cellulose, 3.0 g of magnesium stearate and 60 g of lactose and further mixing. This mixture was then formed into tablets using a single-run tablet making machine to produce tablets having a diameter of 7 mm and weight of 100 mg.

Example 7

2.5 g of the derivative of the present invention were heated at 122° C. and dissolved in 200 g of TO-10M (nonionic surface activator, Nikko Chemicals Ltd.). 4.7975 liters of sterile physiological saline warmed to 60° C. were added to this solution and stirred well. The resulting liquid was then aseptically distributed into vials and sealed to produce an injection preparation.

Example 8

Water was added to 100 parts by weight of gelatin and 35 parts by weight of edible glycerine and dissolved by heating at 50°–60° C. to prepare a gelatin film having a viscosity of 20000 cps. Next, 95.1% wheat germ oil, 2.9% vitamin E and 2% of the mixture of the derivatives of the present invention used in Example 1 were mixed to prepare an internal preparation. Capsule forming and drying were performed in accordance with routine methods using these materials to produce soft capsules containing 180 mg of the internal preparation per capsule. Each of said capsules contained 3.6 mg of the mixture of derivatives of the present invention and 2.34 mg of α-tocopherol.

Example 9

Stroke-prone SHR rats (SHRSP) (males, 8 weeks old) were divided into 2 groups of 8 rats each. One group was given a normal diet (control group) and the other group a sesamin-containing diet (sesamin group). Rats of the control group were fed commercially available powdered diet (Funabashi SP, Funabashi Nojo Co., Ltd.). Rats of the sesamin group were fed the same diet containing 0.5% of a mixture of the dioxabicyclo[3.3.0]octane derivatives of the present invention (sesamin: 51.1%, episesamin: 47.8% and other dioxabicyclo[3.3.0]octane derivatives: 1.1%). After housing for 8 weeks, the effects on blood pressure, body weight and brain weight, as well as the formation of encephalomalacia, were investigated. Those results are shown in Table 4. Increases in brain weight were observed in SHRSP rats of the control group, while encephalomalacia, a lesion indicative of stroke, was observed in half of those rats. There were no increases in brain weight in rats of the sesamin group, however, and the formation of lesions associated with stroke was also not observed.

TABLE 4

|  | Control Group | Sesamin Group |
|---|---|---|
| Body weight (g) | 255 ± 13 | 252 ± 4 |
| Blood Pressure (mmHg) | 267 ± 7 | 260 ± 7 |
| Brain Weight (g) | 2.02 ± 0.09 | 1.80 ± 0.08 |
| Stroke Incidence (%) | 50 (4/8)[1] | 0 (0/8) |

[1]No. of rats suffering strokes/Total no. of rats

We claim:

1. A method for preventing or alleviating cerebral apoplexy caused by hypertension in a patient comprising administering to a patient a dioxabicyclo[3.3.0]octane derivative represented by the following general formula:

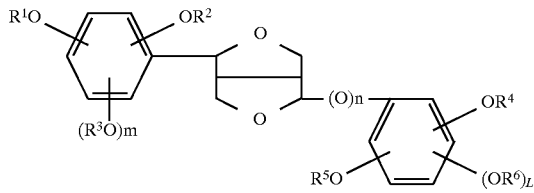

wherein $R^1$, $R^2$, $R^3$, $R^4$, $R^5$ and $R^6$ are respectively and independently a hydrogen atom or an alkyl group having 1–3 carbon atoms, or $R^1$, and $R^2$ and/or $R^4$ and $R^5$ collectively represent a methylene group, and n, m and L represent 0 or 1, in an amount effective for preventing or alleviating cerebral apoplexy caused by hypertension.

2. The method according to claim 1, wherein the dioxabicyclo[3.3.0]octane derivative is administered in the form of a pharmaceutical composition.

3. The method according to claim 1, wherein the dioxabicyclo[3.3.0]octane derivative is administered in the form of a food or beverage.

4. The method according to claim 1, wherein said dioxabicyclo[3.3.0]octane derivative is sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, or 2-(3,4-methylenedioxyphenyl-6-(3-methoxy-4-hydroxyphenoxy)-3,7-dioxabicyclo[3.3.0]octane.

5. The method according to claim 1, wherein the dioxabicyclo[3.3.0]octane derivative is administered in the form of an extract which comprises the derivative as its active ingredient.

6. The method according to claim 1, wherein the derivative is administered orally or parenterally.

7. The method according to claim 1, wherein between 1 mg and 10 g of the derivative is administered per day to the patient.

8. The method according to claim 7, wherein between 1 mg and 2 g of the derivative is administered per day to the patient.

9. The method according to claim 8, wherein between 1 mg and 200 mg of the derivative is administered per day to the patient.

10. The method according to claim 1, wherein said dioxabicyclo[3.3.0]octane derivative is administered in the form of a pharmaceutical composition comprising sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, or 2-(3,4-methylenedioxyphenyl-6-(3-methoxy-4-hydroxyphenoxy)-3,7-dioxabicyclo[3.3.0]octane.

11. The method according to claim 1, wherein said dioxabicyclo[3.3.0]octane derivative is administered in the form of a food or beverage comprising sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, or 2-(3,4-methylenedioxyphenyl-6-(3-methoxy-4-hydroxyphenoxy)-3,7-dioxabicyclo[3.3.0]octane.

12. The method according to claim 1, wherein said dioxabicyclo[3.3.0]octane derivative is administered in the form of a food or beverage to which sesamin, sesaminol, episesamin, episesaminol, sesamolin, 2-(3,4-methylenedioxyphenyl)- 6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, or 2-(3,4-methylenedioxyphenyl-6-(3-methoxy-4-hydroxyphenoxy)-3,7-dioxabicyclo[3.3.0]octane, or an extract comprising as its active ingredient one or a plurality of said compounds either alone or in the form of a mixture, has been added.

13. The method according to claim 1, wherein from 1 mg to 10 g of one or more of the compounds selected from the group consisting of sesamin, sesaminol, episesamin, episesaminol, sesamolin, 2-(3,4-methylenedioxyphenyl)-6-(3-methoxy4-hydroxyphenyl)-3,7-dioxabicyclo[3.3.0]octane, 2,6-bis-(3-methoxy-4-hydroxyphenyl)-3,7-dioxabicyclo[3.3.0]octane and 2-(3,4-methylenedioxyphenyl)-6-(3-methoxy-4-hydroxyphenoxy)-3,7-dioxabicyclo[3.3.0]octane is administered to said patient.

14. The method according to claim 1, wherein said dioxabicyclo[3.3.0]octane derivative is administered by adding sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, 2-(3,4-methylenedioxyphenyl)-6-(3-methoxy4-hydroxyphenoxy)-3,7-dioxabicyclo[3.3.0]octane, or an extract comprising as its active ingredient one or a plurality of said compounds either alone or in the form of a mixture, to a food or beverage essentially not containing sesamin, sesaminol, episesamin, episesaminol, sesamolin, 2-(3,4-methylenedioxyphenyl)-6-(3-methoxy4-hydroxyphenyl)-3,7-dioxabicyclo[3.3.0]octane, 2,6-bis-(3-methoxy-4-hydroxyphenyl)-3,7-dioxabicyclo[3.3.0]octane, and 2-(3,4-methylenedioxyphenyl)-6-(3-methoxy-4-hydroxyphenoxy)-3,7-dioxabicyclo[3.3.0]octane, and administering said food or beverage to said patient.

* * * * *